United States Patent [19]

Blaffert et al.

[11] Patent Number: 5,039,409
[45] Date of Patent: Aug. 13, 1991

[54] CHROMATOGRAPHY APPARATUS

[75] Inventors: Thomas Blaffert, Hamburg, Fed. Rep. of Germany; Nicholas C. Dunand, Cambridge, England; Petrus J. Schoenmakers, Eindhoven, Netherlands

[73] Assignee: U.S. Philips Corporation, New York, N.Y.

[21] Appl. No.: 406,924

[22] Filed: Sep. 13, 1989

[30] Foreign Application Priority Data

Sep. 14, 1988 [GB] United Kingdom ............... 8821559
Dec. 14, 1988 [GB] United Kingdom ............... 8829153
May 5, 1989 [GB] United Kingdom ............... 8910340

[51] Int. Cl.[5] ............................................. B01D 15/08
[52] U.S. Cl. .............................. 210/198.2; 73/61.1 C; 364/497
[58] Field of Search .................... 364/497, 498, 502; 422/70; 73/61.1 C; 210/198.2

[56] References Cited

U.S. PATENT DOCUMENTS

| | | | |
|---|---|---|---|
| 3,728,526 | 4/1973 | Youngblood | 364/502 |
| 3,917,531 | 11/1975 | Magnussen | 417/20 |
| 3,985,021 | 10/1976 | Achener et al. | 73/61.1 C |
| 4,233,156 | 11/1980 | Tsukada et al. | 73/61.1 C |
| 4,364,263 | 12/1982 | Sankoorikal et al. | 210/198.2 |
| 4,482,966 | 11/1984 | Mito et al. | 364/498 |
| 4,579,663 | 4/1986 | Poile et al. | 210/198.2 |
| 4,592,842 | 6/1986 | Tomlinson | 210/198.2 |
| 4,595,496 | 6/1986 | Carson | 210/198.2 |
| 4,631,687 | 12/1986 | Kowalski et al. | 73/61.1 C |
| 4,728,434 | 3/1988 | Trafford | 210/198.2 |
| 4,740,903 | 4/1988 | Nakatsuka et al. | 364/497 |
| 4,772,388 | 9/1988 | Allington | 210/198.2 |
| 4,900,435 | 2/1990 | Anderson | 210/198.2 |
| 4,927,532 | 5/1990 | Pospisil et al. | 210/198.2 |
| 4,941,101 | 7/1990 | Crilly | 364/498 |

OTHER PUBLICATIONS

*Introduction to Modern Liquid Chromatography*, Snyder & Kirkland, 2nd ed., Wiley & Sons (1979), p. 130.

Primary Examiner—Stanley S. Silverman
Assistant Examiner—Cynthia L. Nessler
Attorney, Agent, or Firm—Paul R. Miller

[57] ABSTRACT

Chromatography apparatus capable of deriving optimum conditions for an analysis includes data processing means which comprises calculating means (20) to be supplied with initial conditions (24) entered by the chromatographer and which may be calculated from the results of an initial chromatogram, limits and requirements (25) relating to limiting values of parameters of the chromatograph and to the required selectivity and sensitivity of the analysis and which are entered by the chromatographer, and the detector time constant (23) which is selectable, within limits, by the chromatographer. The data processing means also includes a column data base (21) which contains data specifying the available separating columns and a detector data base (22) which contains data specifying the available detectors.

The optimization criteria are the minimum possible analysis time coupled with adequate peak separation and sensitivity. The optimum conditions are obtained by calculating maximum mobile phase flow rates which produce the required peak separation and sensitivity with each available separating column, detector, time constant combination and selecting that combination which allows the fastest analysis (26). The conditions may either be automatically set up or indicated to the chromatographer by means of a display unit, or a hard copy may be produced by a printer.

The parameters which limit the speed of analysis are indicated to the chromatographer to enable conditions to be relaxed, under the control of the chromatographer, if that is considered acceptable in order that a faster analysis may be achieved.

15 Claims, 10 Drawing Sheets

Fig. 2.

| COLUMN NUMBER | LENGTH L (mm) | DIAMET $d_c$ (mm) | PARTICLE SIZE $d_p$ (μm) | POROSITY $\varepsilon$ | EFFICIENCY FACTOR $\eta$ | PERMEABILITY FACTOR $\phi$ | PRESSURE DROP $P_{col}$, min | $P_{col}$, max | FLOW RATE $F_{col}$, min | $F_{col}$, max | SAMPLE SIZE $Q_{col, max}$ |
|---|---|---|---|---|---|---|---|---|---|---|---|
| 1 | 300 | 4.6 | 10 | 0.63 | 1.0 | 1.0 | 6 | 61 | 0.08 | 6.4 | 0.24 |
| 2 | 150 | 4.6 | 5 | 0.61 | 1.0 | 1.0 | 25 | 246 | 0.16 | 12.8 | 0.24 |
| 3 | 100 | 4.6 | 3 | 0.58 | 0.9 | 1.1 | 83 | 834 | 0.27 | 21.3 | 0.24 |
| 4 | 250 | 4.6 | 8 | 0.63 | 1.0 | 1.0 | 10 | 100 | 0.1 | 8.0 | 0.24 |
| 5 | 250 | 2.0 | 8 | 0.63 | 1.0 | 1.1 | 11 | 110 | 0.02 | 1.5 | 0.04 |
| 6 | 250 | 1.0 | 8 | 0.63 | 0.9 | 1.2 | 12 | 120 | 0.004 | 0.4 | 0.02 |

Fig.4a.

| EQN. NR | RELATIONSHIP |
|---|---|
| 1 | $u \propto \dfrac{F}{\varepsilon d_c^2}$ |
| 2 | $Q \propto \dfrac{V_{inj}}{D_p}$ |
| 3 | $t \propto \dfrac{L}{u}$ |
| 4 | $\Delta p \propto \dfrac{\phi L u}{d_p^2}$ |
| 5 | $N \propto \dfrac{\eta L}{u\, d_p}$ |
| 6 | $h \propto \dfrac{B Q \sqrt{N}}{d_c^2 \varepsilon L}$ |
| 7 | $V_{det.\,max} \propto \dfrac{F t}{\sqrt{N}}$ |
| 8 | $\tau_{max} \propto \dfrac{t}{\sqrt{N}}$ |
| 9 | $R_s \propto \sqrt{N}$ |
| 10 | $n \propto \dfrac{\gamma}{\sqrt{\tau}}$ |
| 11 | $SNR \propto \dfrac{h}{n}$ |

Fig. 4b.

| SYMBOL | RELATIONSHIP |
|---|---|
| $d_c$ | COLUMN DIAMETER |
| $dp$ | PARTICLE SIZE |
| $h$ | PEAK HEIGHT |
| $n$ | NOISE |
| $\Delta p$ | PRESSURE DROP |
| $t$ | RETENTION TIME |
| $u$ | LINEAR VELOCITY |
| $F$ | FLOW RATE |
| $L$ | COLUMN LENGTH |
| $N$ | NUMBER OF THEORETICAL PLATES |
| $Q$ | SAMPLE SIZE (MASS UNITS) |
| $R_s$ | RESOLUTION |
| SNR | SIGNAL-TO-NOISE RATIO |
| $V_{det.max}$ | HIGHEST PERMISSABLE DETECTOR-CELL VOLUME |
| $V_{inj}$ | INJECTION VOLUME |
| $\beta$ | DETECTION SENSITIVITY FACTOR |
| $\gamma$ | DETECTION NOISE FACTOR |
| $\varepsilon$ | COLUMN POROSITY |
| $\eta$ | COLUMN EFFICIENCY FACTOR |
| $\tau_{max}$ | HIGHEST PERMISSABLE DETECTION TIME CONSTANT |
| $\phi$ | COLUMN PERMEABILITY FACTOR |

Fig. 5.

| EQN. NR | RELATIONSHIP |
|---|---|
| (12) | $t = c_{12} \dfrac{L \varepsilon d_c^2}{F}$ |
| (13) | $F2 = c_{13} \dfrac{d_p^2 \varepsilon d_c^2}{\phi L} \Delta p$ |
| (14) | $F3 = c_{14} \dfrac{\eta L \varepsilon d_c^2}{d_p} \dfrac{1}{R_s^2}$ |
| (15) | $F4 = c_{15} \dfrac{\beta^2 Q^2 \eta \tau}{\gamma^2 d_c^2 \varepsilon L d_p} \dfrac{1}{SNR^2}$ |
| (16) | $F5 = c_{16} \dfrac{L \varepsilon d_c^2}{\eta} \dfrac{1}{\tau^2_{max}}$ |
| (17) | $F6 = c_{17} \dfrac{\eta}{L d_p \varepsilon d_c^2} v^2_{det\,max}$ |

SYSTEM INPUT PARAMETERS

PEAKTABLE, i.e. FOR EACH PEAK
    RETENTION TIME
    PEAK HEIGHT*
    PEAK WIDTH (OR PLATE COUNT)*
    ASYMMETRY FACTOR *
UNRETAINED TIME
SAMPLE SIZE (INJECTION VOLUME AND DILUTION FACTOR)
NOISE

---

*OPTIONAL. IF NO VALUES FOR THE PEAK WIDTHS ARE PROVIDED,
A VALUE FOR THE COLUMN PLATE COUNT IS NEEDED

---

LIMITS AND REQUIREMENTS

REQUIRED RESOLUTION
REQUIRED SIGNAL-TO-NOISE RATIO (SNR)
MINIMUM AND MAXIMUM FLOW RATE
MINIMUM AND MAXIMUM PRESSURE DROP

---

SYSTEM OUTPUT PARAMETERS

PREDICTED VALUES FOR THE ANALYSIS TIME, RESOLUTION, SNR

SELECTED COLUMN
OPTIMUM FLOW RATE (AND RESULTING PRESSURE DROP)
INJECTION VOLUME AND DILUTION FACTOR
DETECTOR (CELL)
ATTENUATION
CHART SPEED
TIME CONSTANT

Fig. 8a.

A. SYSTEM INPUT PARAMETERS

| CHARACTERISTIC | PEAK 0* | PEAK 1 | PEAK 2 |
|---|---|---|---|
| RETENTION TIME (S) | 79 | 91 | 180 |
| PEAK HEIGHT (AU) | 0.01 | 0.6 | 0.4 |
| PLATE COUNT | 23,000 | 23,000 | 23,000 |
| ASYMMETRY FACTOR | 1 | 1 | 1 |

| | |
|---|---|
| UNRETAINED TIME | 79s |
| SAMPLE SIZE | 0.1 µg |
| NOISE (AU) | 0.01 |
| INITIAL COLUMN | nr. 4 |
| INITIAL FLOW RATE | 1 ml/min |
| INITIAL PRESSURE DROP | 50 BAR |
| | |
| DETECTOR (nr. 1) | |
| DETECTOR-CELL VOLUME | 8 µl |
| DETECTOR SENSITIVITY FACTOR ($\beta$) | 1 |
| DETECTOR NOISE FACTOR ($\gamma$) | 1 |
| | |
| ASSESSMENT | |
| INITIAL RESOLUTION ($R_s$, min) | 5.29 |
| SIGNAL-TO-NOISE RATIO (SNR) | 400 |

B. LIMITS AND REQUIREMENTS

| | |
|---|---|
| REQUIRED RESOLUTION | 1.5 |
| REQUIRED SIGNAL-TO-NOISE RATIO (SNR) | 80 |
| MINIMUM AND MAXIMUM FLOW RATE | 0.1 - 4 ml/min |
| MINIMUM AND MAXIMUM PRESSURE DROP | 10 - 250 BAR |
| MAXIMUM SAMPLE SIZE | 1 µg |
| DETECTION TIME CONSTANT | 20, 50, 100 ms |

*Small peak assumed to be present at $t = t_0$

Fig.8b.

C. SPECIFIED COLUMN LIMITS

| COLUMN NR. | Fmin ml/min | Fmax ml/min | Pmin bar | Pmax bar | Qmax µg |
|---|---|---|---|---|---|
| 1 | 0.08 | 6.4 | 6 | 61 | 0.24 |
| 2 | 0.16 | 12.8 | 25 | 246 | 0.24 |
| 3 | 0.27 | 21.3 | 83 | 834 | 0.24 |
| 4 | 0.10 | 8.0 | 10 | 100 | 0.24 |
| 5 | 0.02 | 1.5 | 11 | 110 | 0.04 |
| 6 | 0.004 | 0.4 | 12 | 120 | 0.02 |

D. SYSTEM OUTPUT PARAMETERS

| | |
|---|---|
| OPTIMUM COLUMN | nr. 2 |
| PREDICTED ANALYSIS TIME $t_2$ | 34s |
| PREDICTED SIGNAL-TO-NOISE RATIO | 148 |
| PREDICTED RESOLUTION | 2.90 |
| OPTIMUM FLOW RATE | 3.2 ml min |
| PREDICTED PRESSURE DROP | 246 bar |
| | |
| DETECTOR (nr. 3) | |
| DETECTOR-CELL VOLUME | 1.2 µl |
| DETECTOR SENSITIVITY FACTOR ($\beta$) | 0.6 |
| DETECTOR NOISE FACTOR ($\gamma$) | 2.0 |

E. ADVICE

THE LIMITING FACTOR IS THE PRESSURE DROP OVER THE COLUMN. THE MAXIMUM PRESSURE DROP WILL NEED TO BE INCREASED IF YOU WANT TO REDUCE THE ANALYSIS TIME FURTHER.

CHROMATOGRAPHY APPARATUS

DESCRIPTION

The invention relates to chromatography apparatus.

The requirements for an ideal chromatographic separation from a user's point of view are (i) sufficient separation and (ii) sufficient sensitivity in (iii) the shortest possible time. In order to achieve this, the retention needs to be brought into the optimum range and the chromatographic selectivity either needs to be adequate from the start or optimised. Methods of optimisation of selectivity are disclosed in, for example "The optimisation of chromatographic selectivity; A guide to method development" by P. J. Schoenmakers published by Elsevier, Amsterdam, 1986. Retention (in terms of capacity factors) and selectivity is controlled by the nature and composition of the mobile and stationary phases and by physical parameters such as temperature and pH. However, even when a phase system has been selected and all the physical parameters have been fixed, the chromatographer is left with many choices ("chromatographic parameters") that may affect the outcome of the separation with respect to the three criteria (or "analytical goals") listed above. The most important chromatographic parameters in high-pressure liquid chromatography (HPLC) are a) column dimensions (length, diameter, particle size),
b) operating conditions (flow rate, attenuation),
c) sample parameters (injection volume, dilution factor), and
d) the instrument.

The instrument should be compatible with the selected column, operating conditions, and the sample. Among the relevant aspects of the instrumentation are the external dispersion; flow and pressure ranges; and the sensitivity, noise, and time constant of the detection. If insufficient attention is paid to instrumental parameters, good chromatographic separations may not be achieved.

If the chromatographer is able to make all the right choices for the chromatographic parameters, significant improvements can be made towards the achievment of the three analytical goals. Unfortunately, making all the right choices is very difficult, due to the many interdependencies between the numerous different parameters. A reasonably complete but concise description of the subject of chromatographic optimisation "High performance liquid chromatography" Vol. 2, pp 1-56. editor Cs. Horvath, Academic Press, New York, 1980, may transfer the required knowledge from an expert (author) to a user (reader). However, much effort is required from the user to read and digest the knowledge and then to apply it in the correct manner. As a consequence, most separations are performed at conditions far removed from the optimum and the chromatographer achieves much less than what is theoretically and practically possible.

One way to cope with the complexity of chromatographic optimisation is the use of a simulation program as disclosed in an article entitled "Computer Simulation as a Means of Developing an optimised Reversed-Phase Gradient-Elution Separation" by J. W. Dolan, L. R. Snyder and M. A. Quarry published in Chromatographia 24 (1987) pp 261-276. This allows the user to study the effects of changes in various parameters on the resulting chromatogram, without having to perform experiments. As such, simulation programs can be excellent learning tools. The programs can also be used to yield a satisfactory solution to a given separation problem. What a simulation program will not do, however, is provide the best or optimum solution to the problem.

It is an object of the invention to enable the provision of chromatography apparatus capable of helping a chromatographer to perform a given separation under optimum conditions within the constraints of available instrument components.

The invention provides chromatography apparatus including means for determining optimum conditions for producing a chromatographic separation of the components of a sample using a given chromatography system wherein the apparatus further includes means for indicating which requirement or system parameter limits the speed of production of the chromatogram.

In this way in addition to producing information enabling a global optimum analysis to be made within the constraints of the available apparatus, the chomatographer can be informed which constraint is limiting the speed of analysis. Some constraints which have been specified may, under the control of the chromatographer, be relaxed. For example, if the factor limiting the speed of analysis is the desired signal-to-noise ratio, the chromatographer may choose to reduce the required ratio in order to speed the analysis. However, if other instrumental constraints are limiting the speed of analysis, such as the maximum flow rate the pump can deliver, then no further increase in the speed of analysis can be achieved with the available equipment. However, such information may be useful to the chromatographer when considering the purchase of new or replacement component parts of the apparatus since a higher specified component may enable certain types of analyses to be carried out more quickly.

The means for determining optimum conditions may be an expert system which may be configured as described hereinafter. The expert system is arranged to provide an explanation of its recommendations and may also offer additional advice or assistance when prompted by the user.

The expert system selects the optimum column from a user-defined column data base and suggests the optimum operating conditions (flow rate, sample size) and instrumentation (detector cell, time constant). The optimum separation is defined as the one yielding (i) sufficient separation and (ii) sufficient sensitivity in (iii) the shortest possible time. On a given column, the shortest possible time corresponds to the highest possible flow rate. The optimization is performed by calculating the highest permissible flow rates (ceilings) with regard to seven different parameters and the lowest permissible flow rates (floors) with regard to five other parameters. A valid result is obtained if the lowest ceiling is higher than the highest floor.

An explanation of the optimization process can be obtained for each column in combination with the optimum detector (cell) and detection time constant. If only one column is considered, the explanation can be obtained for each column - detector - time-constant combination, no matter whether a valid result is obtained or not. The explanation may be provided in the form of a bar chart, depicting all the different floors and ceilings. This allows the user to rapidly identify which factor or factors limit the speed of the analysis. Further advice to the user may be available for each of the twelve parameters, as described in the embodiment, considered during the optimization. This may help the user to relax the constraints imposed by the limiting factor or factors and hence to reduce the analysis time.

One of the requirements may be the peak separation, in which case the apparatus may include means for enabling the chromatographer to specify the minimum acceptable peak separation.

One of the requirements may be the sensitivity or signal-to-noise ratio of the chromatogram, in which case the apparatus may include means for enabling the chromatographer to specify the minimum acceptable sensitivity or signal-to-noise ratio.

The system parameters may include the detector time constant. The chromatography apparatus may include means for selecting the detector time constant. The chromatography apparatus may include memory means for storing data specifying each of the available separating columns and may also include memory means for storing data specifying each of the available detectors. The chromatography apparatus may comprise chromatography structure including a pump for delivering a mobile phase at a desired flow rate and pressure to the separating column.

The system parameters may include the maximum and minimum mobile phase flow rates deliverable by the pump, and may also include the maximum and minimum pressures at which the pump is capable of delivering the mobile phase. The memory means may store data specifying each of the available mobile phase delivery pumps.

The means for indicating which requirement or system parameter limits the speed of production of the chromatogram comprises means for displaying as a bar chart the maximum and minimum flow rates associated with the requirements and system parameters. In this way the chromatographer can see simultaneously all the factors which limit the speed of analysis and can determine whether a relaxation in any given constraint will enable a significantly faster analysis to be performed.

An embodiment of the invention will now be described, by way of example, with reference to the accompanying drawings in which:

FIG. 1 shows in diagrammatic form liquid chromatography apparatus according to the invention, FIG. 2 shows an example of a separating column data base, FIG. 3 shows the organisation of data processing apparatus forming part of the liquid chromatography apparatus of FIG. 1, FIG. 4a shows a first set of equations for use in the data processing apparatus in performing the method according to the invention, FIG. 4b shows a set of parameters for use in the data processing apparatus according to the present invention, FIG. 5 shows a further set of relationships for use in a data processing apparatus in performing the method according to the present invention, FIG. 6 is a flow diagram illustrating a procedure with the method according to the invention, FIG. 7 shows a summary of system input parameters and limits and requirements which are used in conjunction with the column and detector data bases to produce an optimum analysis and the parameters produced by the data processing arrangement to enable the chromatographer to perform an optimum analysis, FIGS. 8a and 8b illustrate a particular example of an optimisation of an experimentally produced chromatogram, and FIG. 9 shows a bar chart illustrating maximum and minimum flow rates associated with various instrument parameters and analytical requirements.

FIG. 1 shows an embodiment of the invention in the form of a liquid chromatograph apparatus comprising a reservoir 1 for the mobile phase and a pump 2 for pumping the mobile phase at a desired flow rate through a separating column 3 to a detector 4. A sample injector 5 is connected between the outlet of the pump 2 and the inlet of the column 3 to enable a sample which is to be chromatographically separated to be applied to the column. The detector 4, which will include a detector flow cell through which the column eluent flows, is arranged to produce an electrical signal which is dependent on the composition of the eluent flowing through the cell. The electrical output of the detector 4 is fed to a computer 6 which is arranged to produce information for display on a display unit 7, for example a video display unit. The display unit 7 is also provided with a keyboard for entering data into the computer 6.

The components making up the liquid chromatograph which performs the chromatographic separation are contained within the dotted box 8. Components of a sample injected into the separating column 3 via the sample injector 5 are detected by the detector 4 which produces a chromatogram showing the separated component peaks. When the chromatographer has selected the parameters to provide adequate retention and selectivity and optimised them, if desired, an initial chromatogram is obtained which is entered into the computer 6 where it is evaluated and the parameter values used to obtain the chromatogram are processed. The computer 6 is provided with a data base defining the available separating columns and detectors. A typical column data base is given in FIG. 2.

The computer 6 is organised as shown in FIG. 3 which shows diagrammatically the input data used to perform calculations and the data produced as a result of the calculations. In FIG. 3 the box 20 represents the central processing unit which performs calculations using data stored in a data base and various conditions relating to a specific analysis to be performed entered by a user. Box 21 represents the separating column data base which may be of the form shown in FIG. 2. Box 22 represents the detector data base which similarly specifies the parameters of the available detectors. Box 23 represents all the possible detector time constants. Box 24 represents initial conditions which are produced from an assessment of the initial chromatogram. Box 25 represents limits and requirements which are set by the chromatographer and entered on the keyboard. Box 26 represents the optimum operating conditions which are obtained as a result of the calculations and are the outputs of the computer 6.

The initial conditions represented by Box 24 are obtained from the initial chromatogram which is assessed to produce three values. These are i) the overall analysis time $t_{ini}$ obtained from a measurement of the retention times of the individual component peaks; ii) the resolution $R_{s,ini}$ of the chromatogram, which is calculated from the widths and distances between each pair of peaks; and iii) the sensitivity or the signal-to-noise ratio $SNR_{ini}$ of the chromatogram which is a measure of the difference between the peak heights and noise spikes in the system. Also included in the initial conditions are the instrument parameters used to produce the initial chromatogram and these may be entered by the chromatographer using the keyboard. These will normally be merely a record of which column and detector were used, rather than detailing the parameters of the column and detectors since these parameters are already available to the computer 6 from the column and detector data bases. Further information entered by the chromatographer will include the mobile phase composition and flow rate used to obtain the initial chromatogram.

The detector data base represented by Box 22 contains data representing each of the detectors which are available. There are three particular factors which influence the quality of the chromatogram. These are the detector volume $V_{det}$, which affects the dispersion (the larger the volume the wider the peaks become); the sensitivity factor $\beta$ and the noise factor $\alpha$ which represents the differences in noise produced by different detectors under identical conditions.

The possible detector time constants $\tau$ represented by Box 23 are a measure of the speed with which the detector responds to a signal. They can alternatively be considered as the bandwidth of the detector. Typically detector time constants lie in a range between 20 msecs and 100 msecs and can be selected in discrete steps by the chromatographer. The time constant has two opposing effects on the quality of the chromatogram. As the time constant is increased the dispersion of the chromatogram is increased (broadening the peaks in terms of time) leading to a reduction in the quality of the chromatogram while the effect of noise is decreased leading to an increase in the quality of the chromatogram.

Box 25 represents limits and requirement. The limits include the sample volume, which is the maximum amount of sample which is available for analysis ($Q_{samp,max}$), and the instrumental limits which are principally the maximum and minimum flow rates ($F_{min,inst}$; $F_{max,inst}$) and pressure drops ($\Delta P_{max,inst}$; $\Delta P_{min,inst}$) the instrument can achieve. The requirements are the resolution ($R_{s,req}$) and the signal-to-noise ratio ($SNR_{req}$) the chromatographer desires to achieve for the analysis. The limited sample volume and the instrumental limits are hard physical limits whereas the chromatographer's requirements can be modified to express higher or lower demands for the quality of an analysis.

The Box 20 represents the calculations performed by the computer 6 in order to determine the optimum operating conditions. The complex inter-relationships between the operating parameters are shown in the equations 1 to 11 which are given in FIG. 4a). The symbols used in equations 1 to 11 are defined in FIG. 4b). The relationships given in FIG. 4a) have been taken from the book by P. J. Schoenmakers referred to in the introductory part of this specification. It should be noted that these equations are not the only ones which can be used to express the inter-relationships and that other sets of equations could be substituted to give similar results.

There are two main problems for the chromatographer in using these relationships to optimise the chromatogram. First the large number of relationships and secondly the opposing and interactive effects of altering parameters within these relationships. Thus in practice the chromatographer either ignores some of the relations and limitations or, while considering them all, the chromatographer attempts to fix each parameter in turn resulting in a local rather than a global optimum.

In order to obtain a global optimum the following procedure, which is a procedure within the method according to the invention, may be undertaken, as may be seen by the relationship set forth in FIG. 5. Equation 12 can be derived by combining equations 1 and 3 and shows that for a given column/detector/time constant combination the highest attainable flow rate gives the shortest analysis time. This is the requirement iii) in the second paragraph for an optimum analysis. Consequently to obtain the optimum parameters for a given column/detector/time constant combination the highest possible flow rate is found which a) maintains the required sensitivity and separation, i.e. requirements i) and ii) in the second paragraph,
b) respects the hard limits of the system e.g. maximum and minimum flow rates and pressures, and
c) respects the detector limits on dispersion of the chromatogram in terms of the detector cell volume and time constant.

Equations 13 to 17 can be derived from equations 4, 7, 8, 9 and 11, which relate the limits and requirements to the operating parameters, by substitution using equations 1, 2, 5, 6 and 10 where necessary. Equations 13 to 17 are written in terms of flow rate and enable minimum and maximum flow rates to be determined.

FIG. 6 represents the calculation of flow rate limits. Box 100 represents the calculation of a first maximum flow rate $Fl_{max}$ which is the lower of the maximum flow rate the pump 2 is capable of delivering (Box 101) and the maximum flow rate the column can withstand (Box 102). The maximum flow rate of the pump 2 is a hard instrumental limit while the maximum flow rate the column can withstand can be obtained from the column data base. Box 132 represents the calculation of a second maximum flow rate $F2_{max}$. The flow rate F2 is given in equation 13 in terms of a given set of column parameters and the pressure drop. Thus if the pump 2 or other instrumental limitation has an upper pressure drop limit of $P_{inst\ max}$ then this defines an upper flow rate limit. This limit is a hard, instrument limit and is represented by Box 103. Similarly a particular column will have an upper pressure limit as can be seen from FIG. 2 which will again define an upper flow rate limit. The column maximum pressure limit $\Delta P_{col,max}$ is represented by Box 104 and is obtained from the column data base. Box 132 represents the maximum flow rate $F2_{max}$ which is derived from the lower of $\Delta P_{inst,max}$ and $\Delta P_{col,max}$ using equation 13.

Equation 14 can be derived using equations 1, 5 and 9 to give a flow rate F3 in terms of column parameters and resolution. The required resolution is entered by the analyst and is represented by Box 105. Box 106 represents the calculation of the maximum flow rate $F3_{max}$ which enables the entered resolution requirement $R_{s\ req}$ to be achieved using a specified column. A greater flow rate than F3 max will not give suficient separation.

Equation 15, which shows flow rate in terms of a column/detector/time constant combination, sample volume and signal-to-noise ratio or required sensitivity, can be obtained by combining equations 1, 2, 5, 6 and 11. By inspection of equation 15 it can be seen that the higher the sample volume (Q) the higher the signal-to-noise ratio (SNR) can be for a given flow rate. Consequently Q is made as large as possible which is either $Q_{samp,max}$, i.e. limited only by the amount of sample available for the analysis, Box 107, or is $Q_{col,max}$, i.e. the maximum sample volume which can be injected without overloading the column, Box 108. $Q_{samp,max}$ is entered by the chromatographer while $Q_{col,max}$ is obtained from the column data base and is represented by Box 108. The sensitivity required (or $SNR_{req}$) is entered by the chromatographer and is represented by Box 109. Box 110 ($F4_{max}$) represents the solving of equation 15 to determine the maximum value for the flow rate F4. Any value greater than the maximum will result in the sensitivity requirement not being met.

Equation 16 can be derived using equations 1. 3, 5 and 8 and shows the flow rate in terms of detector time constant $\tau$. Time constant distortion is a restriction which is inherent in the detection system of any chromatograph. With all other parameters held constant there is a maximum value for the time constant $\tau_{max}$ beyond which peaks become distorted. The current column parameters are assumed and assuming $\tau_{max}$ is the current $\tau$(Box 111) a value for the maximum flow rate $F5_{max}$ is calculated, Box 112. A flow rate greater than $F5_{max}$ will produce distortion of the peaks.

The maximum flow rates $F1_{max}$ to $F5_{max}$ are then inspected, as represented by Box 113, to obtain the lowest of these values which is then the highest allowable flow rate with the specified parameters.

It is also necessary to ensure that this highest allowable flow rate, i.e. the lowest of $F1_{max}$ to $F5_{max}$, is above certain constraints on the minimum allowable flow rates.

Flow rate F1 besides having a maximum value also has a minimum value. Box 114 represents the minimum flow producable by the instrument, primarily limited by the capability of the pump 2, $F_{inst,min}$ while Box 115 represents the minimum permissible flow rate through the column $F_{col,min}$. Thus $F1_{min}$ is produed in Box 116 in the same way as $F1_{max}$ is produced in Box 100, i.e. the highest of the two minimum flow rates $F_{inst,min}$ and $F_{col,min}$ is produced as $F1_{min}$.

Similarly flow rate F2 also has a minimum value given by minimum allowable instrument and column pressure drops $\Delta P_{inst,min}$ and $\Delta P_{col,min}$. These are shown in Boxes 117 and 118. The minimum flow rate $F2_{min}$ is calculated (Box 119) in the same way as the maximum flow rate $F2_{max}$, Box 102. The value of $F2_{min}$ is consequently the higher of the two values produced using the minimum instrument and column pressures. Any flow rate below $F2_{min}$ is either not physically or reliably possible for the instrument (pump 2) or is not applicable to the column.

Equation 17, which can be derived from equations 1, 3, 5 and 7, shows flow rate F6 in terms of detector cell volume and column parameters. External volume distortion is a restriction on the volume of the detector cell above which peak distortion becomes unacceptable. The current column parameters are used together with the current detector cell volume obtained from the detector data base, Box 123, to perform the calculation of the flow rate $F6_{min}$ using equation 17, Box 120.

The minimum flow rates $F1_{min}$, $F2_{min}$ and $F6_{min}$ are assessed to find the highest minimum flow rate, Box 121, and provided that the lowest of the maximum flow rates $F1_{max}$ to $F5_{max}$ is greater than or equal to the highest of the minimum flow rates $F1_{min}$, $F2_{min}$ and $F6_{min}$ then the column/detector/time constant combination is valid and the optimum conditions are with a flow rate $F_{max}$ which is the lowest of $F1_{max}$ to $F5_{max}$. Since the analysis time can be determined by means of equation 12, the best possible analysis time for a given column/detector/time constant combination can be found.

This process is repeated for all column/detector/time constant combinations and the results stored or produced as a list. The results are then inspected to find the shortest analysis time and the conditions displayed or printed to enable the chromatographer to perform an overall optimum analysis. In a partially or fully automatic system the flow rate can be directly controlled by the computer 6 over path 9. Similarly a column switching arrangement could be used to select the desired column and might be controlled over line 10 and similarly the column outlets could be switched to selected detectors by means of control signals over line 11. Alternatively the chromatography apparatus and conditions are 7, manually set up by the chromatographer using the parameters produced by the computer 6.

The following information can be indicated to the chromatographer.

1) The combination of column, detector and time constant which produces the overall minimum analysis time.
2) The maximum flow rate possible to obtain the chromatogram together with predicted values of the resultant chromatogram, for example resolution, signal-to-noise ratio or sensitivity, peak times, pressure drop.
3) Information on which of the constraints on the chromatographic apparatus is actually limiting the analysis time. For example if the required resolution is preventing a faster analysis the analyst may decide to relax that requirement but if the restraint is $F_{inst,max}$ there is nothing that can be done to further reduce the analysis time with that particular apparatus.

FIG. 7 shows a summary of system input parameters and limits and requirements which are used in conjunction with the column and detector data bases to produce an optimum analysis and the parameters produced by the data processing arrangement to enable the chromatographer to perform an optimum analysis.

FIGS. 8a and 8b illustrate a particular example of an optimisation of an experimentally produced chromatogram, The column data base of FIG. 2 was used for this example and the column used to generate the initial chromatogram was Nr.4.

The results of the chromatogram assessment are listed in the first section of FIG. 8a. In this example a constant plate count (N=23,000) and symmetrical peaks ($A_s$=1) have been assumed. As a result, the minimum resolution in the initial chromatogram was assessed as 5.39, the resolution between the two 'real' peaks (1 and 2) being the limiting factor. The lowest (relevant) signal is that for peak nr.2, for which the signal-to-noise ratio was assessed as 400.

The flow and pressure limits for each column were calculated assuming that the flow is proportional to the square of the column diameter and inversely proportional to the particle size. The pressure drop was calculated from Eqn.(4) in FIG. 4a. The initial column was assumed to have a specified flow range of 0.1 to 8 ml/min and a specified pressure range of 10 to 100 bar. The flow and pressure limits for each column are listed in FIG. 8b Section C). The maximum values specified for a column may be high, but in that case the specified instrumental (or overall) maximum will apply, i.e., the values from FIG. 8a Section b). The maximum sample size was 0.24 μg for 4.60 mm i.d. columns, 0.08 for 2 mm columns and 0.04 for 1 mm columns.

Three detectors were considered with cell volumes, sensitivity factors and noise factors as follows: 8 μl, 1.0 and 1.0 for cell nr.1, 2.4 µl, 0.8 and 1.5 for cell nr.2, and 1.2µl, 0.6 and 2.0 for cell nr.3. Also, three different time constants were allowed, namely 20, 50 and 100 ms.

FIG. 8b Section D) lists the complete set of (predicted) values for the global optimum as can be displayed on the display unit 7. The global optimum is found for column nr.2 and the conditions at which the optimum is reached can be made immediately available in different windows on the screen. FIG. 8b Section E) shows the kind of advice that follows from knowing the limiting factor in the optimisation process.

The chromatographer may proceed from here by changing one of the specified limits, for example by following the suggestion of the system to increase the maximum pressure drop. A next optimisation cycle can be performed very rapidly and conveniently.

The apparatus also enables the chromatographer to establish a local optimum for one particular column. For example, the chromatographer may ask the system the local optimum if the initial column is maintained. The arrangement can provide the full set of data, including flow rate, SNR, etc. Under the present set of conditions, the column pressure drop always turns out to be the limiting factor, except for the last two columns. These narrow-bore columns cannot be used for the present example, because the available detector cells would cause excessive extra-column dispersion. Different results would have been obtained if only detection time constants of 100 and 50 ms had been available. In this case, the time constant becomes the limiting factor for two of the four possible columns.

Figure 1:
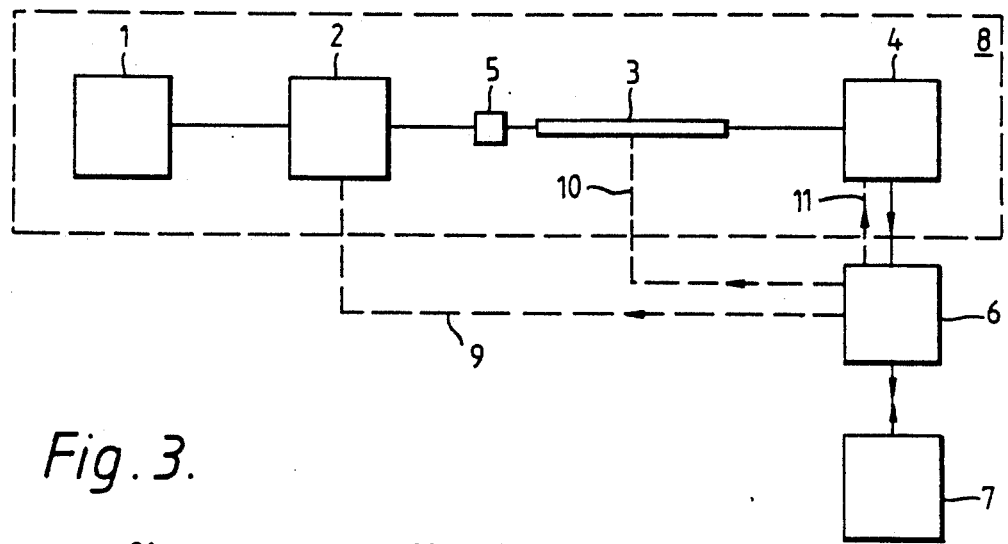
Figure 3:
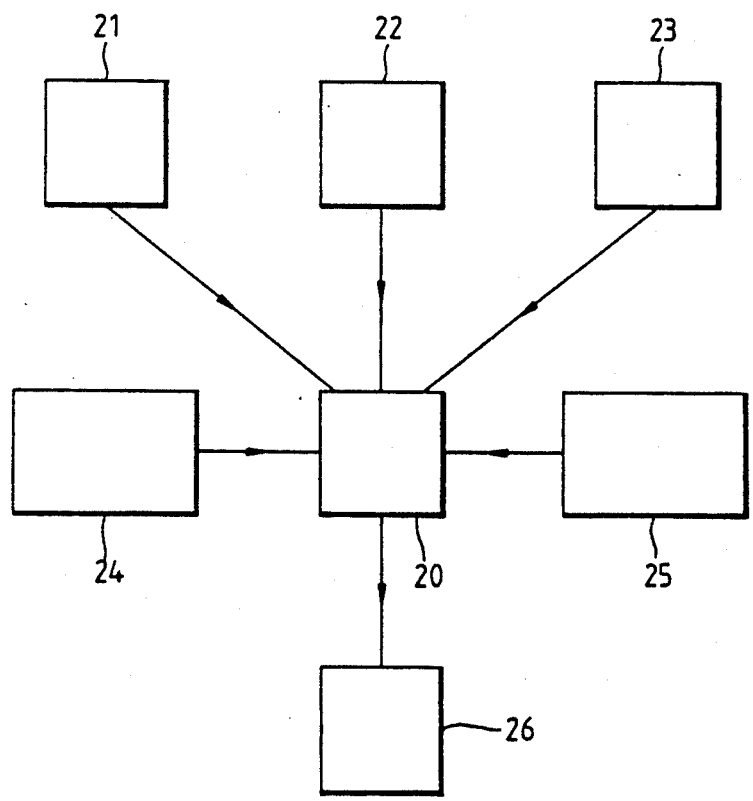
Figure 6:
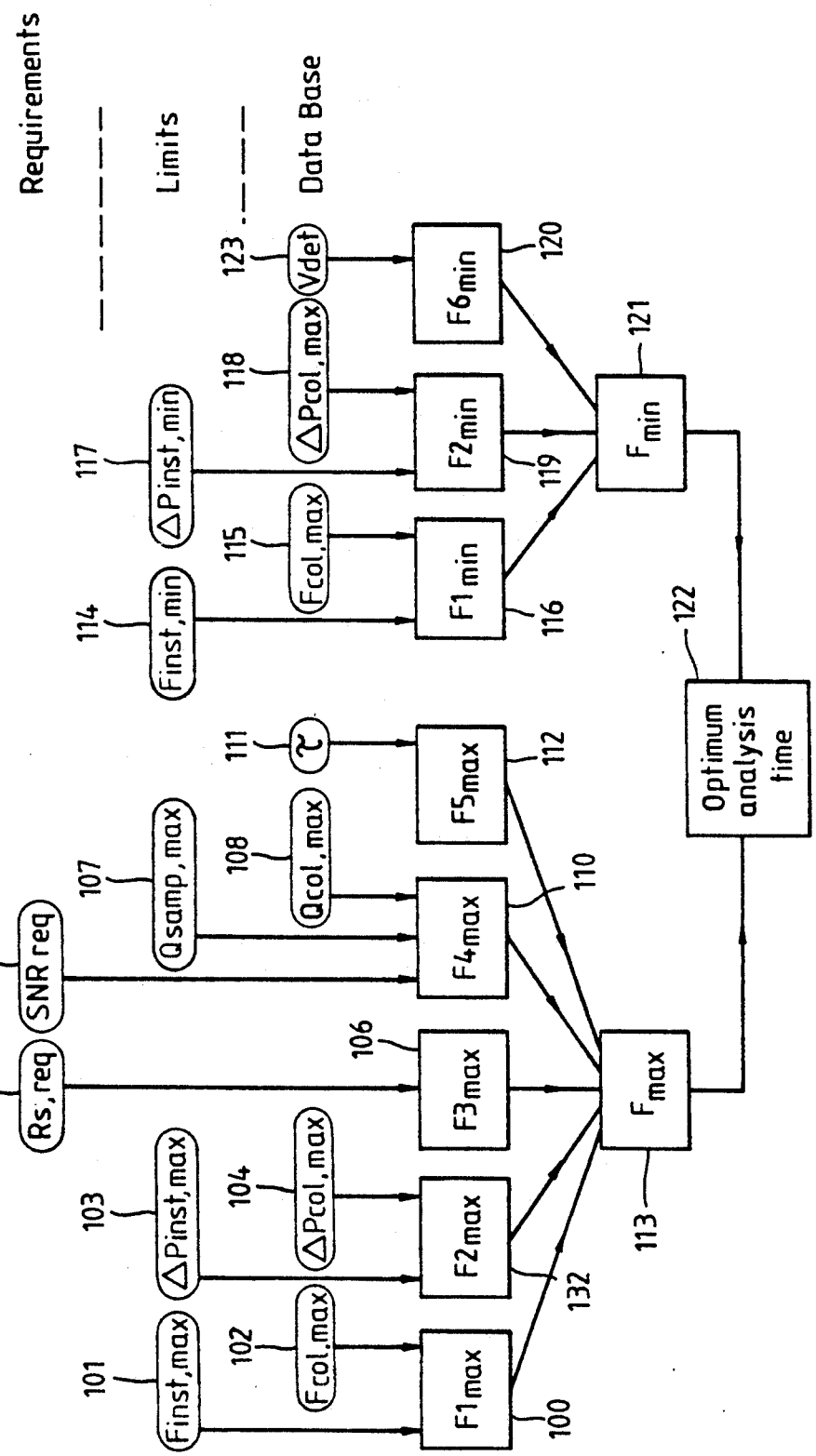
Figure 9:
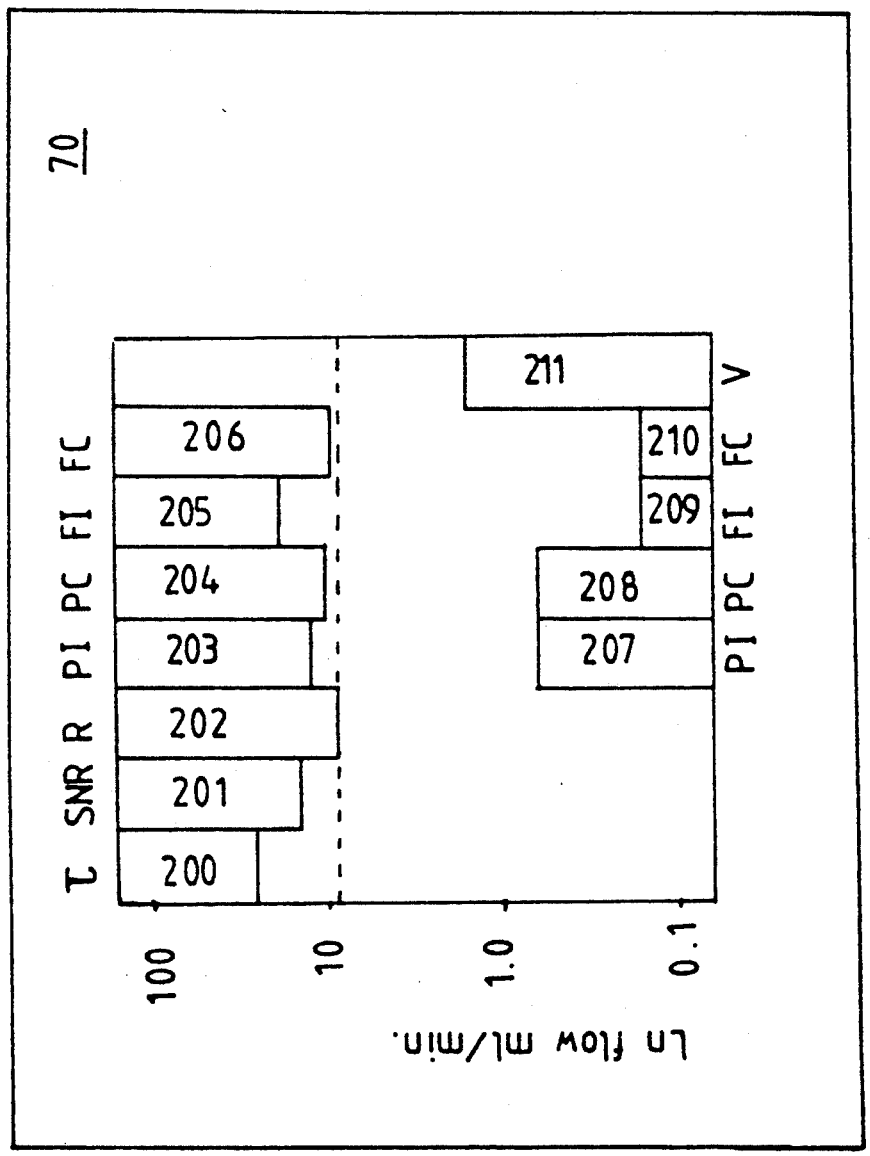

FIG. 9 shows an alternative method of indicating to the chromatographer the requirements or constraints which limit the speed of analysis. The display unit 7, which in this case is in the form of a video display unit, is arranged to display a bar chart of maximum and minimum flow rates determined by the various parameters or instrumental constraints and analytical requirements on a display screen 70. The bar 200 represents the flow rate $F5_{max}$ of FIG. 6 which is dependent on the detector time constant $\tau$. The bar 201 represents the flow rate $F4_{max}$ which is dependent on the required signal to noise ratio $SNR_{req}$. The bar 202 represents the flow rate $F3_{max}$ which is dependent on the required resolution $R_{s.req}$. The bar 203 represents that part of the flow rate $F2_{max}$ which is dependent on the maximum pressure $\Delta P_{inst.max.}$ at which the pump 2 is capable of delivering the mobile phase. The bar 204 represents that part of the flow rate $F2_{max}$ which is dependent on the maximum column pressure $\Delta P_{col.max.}$. Similarly, the bars 205 and 206 represent those parts of the flow rate $F1_{max}$ which are dependent on the maximum flow rate deliverable by the pump $F_{inst.max.}$ and the maximum flow rate through the column $F_{col.max.}$. The bars 207 and 208 represent those parts of the flow rate $F2_{min}$ which are dependent on the minimum pressure at which the pump will deliver the mobile phase $\Delta P_{inst.min.}$ and the minimum column pressure $\Delta P_{col.min.}$. The bars 209 and 210 represent those parts of the flow rate $F1_{min}$ which are dependent on the minimum flow rate deliverable by the pump $F_{inst.min.}$ and the minimum flow rate through the column $F_{col.min.}$. The bar 211 represents the flow rate $F6_{min}$ which is dependent on the detector cell volume $V_{det}$. The dotted line 212 shows the maximum permissible flow rate in order to achieve a satisfactory separation. As can be seen, in the case illustrated in FIG. 9 the limiting factor is the required resolution. If the arrangement shown in FIG. 8B was used this information would be produced in the block headed ADVICE. However, using that arrangement there is no indication as to what improvement in analysis time is possible by relaxing the requirements for resolution in that it is not known what other constraints, if any, are only marginally below that due to the resolution requirement. However, with the bar chart representation as shown in FIG. 9 it is immediately apparent whether by relaxing one constraint a significant increase in flow rate and hence reduction in analysis time can be achieved. Similarly, if an invalid combination is indicated, in which case one or more of bars 207 to 211 will extend above one or more of bars 200 to 206, it can quickly be seen which factor or factors are critical. For example, it may be that the detector volume $V_{det}$ is causing $F6_{min}$ to be greater than one of the maximum flow rates $F1_{max}$ to $F5_{max}$ in which case the choice of a smaller flow cell may enable a valid combination to be achieved.

Although the invention has primarily been described with reference to liquid chromatography apparatus and to a method of analysis by liquid chromatography, it is equally applicable to many forms of chromatographic analysis including gas chromatography although as would be well known to those skilled in the art the relationships between the instrumental parameters would be different. However, similar overall optimisation criteria would apply.

From reading the present disclosure, other modifications will be apparent to persons skilled in the art. Such modifications may involve other features which are already known in the design and use of chromatography apparatus or methods of performing chromatographic separations and component parts thereof and which may be used instead of or in in addition to features already described herein. Although claims have been formulated in the application to particular combinations of features, it should be understood that the scope of the disclosure of the present application also includes any novel feature or any novel combination of features disclosed herein either explicitly or implicitly or any generalisation of one or more of those features which would be obvious to persons skilled in the art, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived therefrom.

We claim:

1. Chromatography apparatus for at least minimizing conditions that limit obtaining of optimum sample information comprising
   (a) first means for producing chromatographic separation of components of a sample,
   (b) second means for detecting said chromatographic separation and for producing electrical signals indicating qualitative and quantitative information about said sample components, and
   (c) third means responsive to both said first means and said second means for determining different operating conditions of said chromatographic separation, said third means further determining those of said operating conditions that limit at least one of speed of analyzing and speed of producing a chromatogram, said third means eliminating one or more of said operating conditions that limit speed of analyzing and speed of producing to control operation of said chromatographic separation, thereby providing optimum information about said sample components from said chromatogram.

2. Chromatography apparatus according to claim 1, wherein said first means includes at least one separating column, and wherein said third means includes memory means for storing data specifying each available separating column.

3. Chromatography apparatus according to claim 1, wherein said second means includes at least one detector, and wherein said third means includes memory means for storing data specifying each available detector.

4. Chromatography apparatus according to claim 1, wherein said first means include pump means for delivering a mobile phase at desired flow rates and at desired pressures to a separating column.

5. Chromatography apparatus according to claim 1, further comprising display means connected to said third means for displaying minimum and maximum values of said operating conditions that limit speed of analysis and speed of producing, wherein said display means display said values in a bar chart format.

6. Chromatography apparatus according to claim 1, wherein said third means includes fourth means for specifying a minimum acceptable peak separation of said chromatogram, and wherein peak separation is an operating condition to be controlled.

7. Chromatography apparatus according to claim 6, wherein said fourth means also specifies a minimum acceptable sensitivity or signal-to-noise ratio, and wherein sensitivity or signal-to-noise ratio is an operating condition to be controlled.

8. Chromatography apparatus according to claim 7, wherein said fourth means also specifies a time constant of said second means for detecting, and wherein a detector time constant is an operating condition to be controlled.

9. Chromatography apparatus according to claim 8, wherein said first means includes at least one separating column, and wherein said third means includes memory means for storing data specifying each available separating column.

10. Chromatography apparatus according to claim 9, wherein said second means includes at least one detector, and wherein said memory means stores data specifying each available detector.

11. Chromatography apparatus according to claim 10, wherein said first means include pump means for delivering a mobile phase at desired flow rates and at desired pressures to a separating column.

12. Chromatography apparatus according to claim 11, wherein said operating conditions to be controlled include maximum and minimum flow rates of said pump means, and wherein said third means controls said flow rates to desired values.

13. Chromatography apparatus according to claim 12, wherein said operating conditions to be controlled include maximum and minimum pressures of said pump means, and wherein said third means controls said pressures to desired values.

14. Chromatography apparatus according to claim 13, wherein said memory means stores data specifying mobile phase conditions of said pump means for each of said desired flow rates and said desired pressures.

15. Chromatography apparatus according to claim 14, further comprising display means connected to said third means for displaying minimum and maximum values of said operating conditions that limit speed of analysis and speed of producing, wherein said display means display said values in a bar chart format.

* * * * *